(12) United States Patent
Peterson et al.

(10) Patent No.: US 10,561,056 B2
(45) Date of Patent: Feb. 18, 2020

(54) SYSTEM AND METHOD FOR MONITORING SOIL CONDITIONS WITHIN A FIELD

(71) Applicant: CNH Industrial America, LLC, New Holland, PA (US)

(72) Inventors: Klint Peterson, Mackinaw, IL (US); Christopher Barrick, Morton, IL (US); John Endsley, Washington, IL (US); James W. Henry, Saskatchewan (CA); Tracey Meiners, Mackinaw, IL (US)

(73) Assignee: CNH Industrial America LLC, New Holland, PA (US)

( * ) Notice: Subject to any disclaimer, the term of this patent is extended or adjusted under 35 U.S.C. 154(b) by 296 days.

(21) Appl. No.: 15/581,614

(22) Filed: Apr. 28, 2017

(65) Prior Publication Data

US 2018/0310465 A1 Nov. 1, 2018

(51) Int. Cl.
*A01B 79/00* (2006.01)
*A01B 49/06* (2006.01)
(Continued)

(52) U.S. Cl.
CPC .......... *A01B 79/005* (2013.01); *A01B 49/027* (2013.01); *A01B 61/046* (2013.01);
(Continued)

(58) Field of Classification Search
CPC ... A01B 79/005; A01B 49/027; A01B 61/046; A01B 63/008; A01B 63/111;
(Continued)

(56) References Cited

U.S. PATENT DOCUMENTS 2,565,668 A   8/1951  Simpson
4,031,963 A   6/1977  Poggemiller et al.
(Continued)

FOREIGN PATENT DOCUMENTS

EP   2462794   6/2012
EP   3050416   8/2016

OTHER PUBLICATIONS

European Search Report for Application No. 18168021.6, dated Oct. 18, 2018, 8 pages.
(Continued)

*Primary Examiner* — Robert E Pezzuto
(74) *Attorney, Agent, or Firm* — Rebecca L. Henkel; Rickard K. DeMille

(57) ABSTRACT

In one aspect, a system for monitoring soil conditions within a field may include an implement configured to be traversed across a field. The implement may further include a plurality of ground engaging tools pivotally coupled to the frame and a plurality of sensors. Each sensor may be configured to detect a parameter indicative of a current position of one of the plurality of ground engaging tools. Additionally, the system may include a controller configured to monitor a displacement of each ground engaging tool and determine a current global ground engaging tool displacement parameter for the implement based on the monitored displacements of the plurality of ground engaging tools. Additionally, the controller may be configured to identify a soil condition for a swath of the field being traversed by the implement based on a comparison between the current global ground engaging tool displacement parameter and a predetermined global displacement threshold.

20 Claims, 9 Drawing Sheets

(51) Int. Cl.
*A01B 63/00* (2006.01)
*A01B 49/02* (2006.01)
*A01B 61/04* (2006.01)
*G01N 33/24* (2006.01)
*A01B 29/04* (2006.01)
*A01B 73/02* (2006.01)
*A01B 63/32* (2006.01)
*A01B 76/00* (2006.01)

(52) U.S. Cl.
CPC ........... *A01B 63/008* (2013.01); *G01N 33/24* (2013.01); *A01B 29/04* (2013.01); *A01B 63/32* (2013.01); *A01B 73/02* (2013.01); *A01B 76/00* (2013.01)

(58) Field of Classification Search
CPC ....... A01B 49/06; A01B 61/044; A01C 7/203; A01C 7/205; A01C 7/201; A01C 7/208; G01N 33/24
USPC ........................ 172/1–11; 701/50; 111/200
See application file for complete search history.

(56) References Cited

U.S. PATENT DOCUMENTS

| | | |
|---|---|---|
| 4,044,838 A | 8/1977 | Wooldridge |
| 4,293,043 A | 10/1981 | Neukom et al. |
| 4,567,689 A | 2/1986 | Lemons |
| 4,723,608 A | 2/1988 | Pearson |
| 4,930,581 A | 6/1990 | Fleischer et al. |
| 5,293,944 A | 3/1994 | Matsumoto |
| 5,390,745 A | 2/1995 | Harden |
| 5,579,850 A | 12/1996 | Kimura et al. |
| 6,041,582 A | 3/2000 | Tiede et al. |
| 6,112,145 A | 8/2000 | Zachman |
| 6,122,145 A | 8/2000 | Zachman |
| 8,083,004 B2 | 12/2011 | Knight, Jr. |
| 8,090,507 B2 | 1/2012 | Yegerlehner et al. |
| 8,201,388 B1 | 6/2012 | Vandeven et al. |
| 8,473,166 B2 | 6/2013 | Zhdanov et al. |
| 8,688,331 B2 | 4/2014 | Peterson et al. |
| 8,827,001 B2 | 9/2014 | Wendte et al. |
| 8,827,011 B2 | 9/2014 | Wendte et al. |
| 8,909,436 B2 | 12/2014 | Achen et al. |
| 9,113,589 B2 | 8/2015 | Bassett |
| 9,232,687 B2 * | 1/2016 | Bassett ................. A01B 61/044 |
| 9,271,440 B2 | 3/2016 | Turko et al. |
| 9,285,501 B2 | 3/2016 | Christy et al. |
| 9,433,142 B2 | 9/2016 | Bergen et al. |
| 9,675,004 B2 * | 6/2017 | Landphair ............... A01C 5/062 |
| 2010/0198529 A1 | 8/2010 | Sauder et al. |
| 2013/0032363 A1* | 2/2013 | Curry ..................... A01B 63/24 172/4 |
| 2013/0046419 A1 | 2/2013 | Anderson et al. |
| 2013/0345937 A1 | 12/2013 | Strelioff et al. |
| 2014/0048295 A1* | 2/2014 | Bassett .................. A01C 7/205 172/2 |
| 2014/0116735 A1 | 5/2014 | Bassett |
| 2015/0305226 A1 | 10/2015 | Zemenchik |
| 2015/0334914 A1 | 11/2015 | Zielke |
| 2015/0378362 A1 | 12/2015 | Hulin |
| 2016/0029547 A1 | 2/2016 | Casper et al. |

OTHER PUBLICATIONS

TruSet Technology—John Deere TruSet Technology Available on John Deere 2730 Combination Ripper Dated Aug. 25, 2015 (2 pages).
Research Gate Publications An Adaptable Tillage Depth Monitoring System for Tillage Machine Dated Nov. 2016 (3 pages).

* cited by examiner

SYSTEM AND METHOD FOR MONITORING SOIL CONDITIONS WITHIN A FIELD

FIELD

The present subject matter is generally directed to agricultural implements and, more particularly, to systems and methods for monitoring displacements of a plurality of ground engaging tools of an agricultural implement to allow soil conditions for a swath of a field traversed by the agricultural implement to be identified.

BACKGROUND

It is well known that, to attain the best agricultural performance from a field, a farmer must cultivate the soil, typically through a tillage operation. Modern farmers perform tillage operations by pulling a tillage implement behind an agricultural work vehicle, such as a tractor. Tillage implements typically include a plurality of ground engaging tools configured to penetrate the soil to a particular depth. In this respect, the ground engaging tools may be pivotally coupled to a frame of the tillage implement. Tillage implements may also include biasing elements, such as springs, configured to exert biasing forces on the ground engaging tools. This configuration may allow the ground engaging tools to maintain the particular depth of soil penetration as the agricultural work vehicle pulls the tillage implement through the field. Additionally, this configuration may also permit the ground engaging tools to pivot out of the way of rocks or other impediments in the soil, thereby preventing damage to the ground engaging tools or other components on the implement.

When performing a tillage operation, it is desirable to create a level and uniform layer of tilled soil across the field to form a proper seedbed for subsequent planting operations. However, firm or compacted soil in certain portions of the field may exert a great enough force on the ground engaging tools to overcome the biasing force of the ground engaging tools. As such, the ground engaging tools may pivot relative to the implement frame as tillage implement is traversed over the field, which result in an uneven seedbed. In such instances, the operator of the tillage implement may not aware of the uneven nature of the seedbed or other soil conditions within the field.

Accordingly, an improved system and method for monitoring soil conditions within a field would be welcomed in the technology

BRIEF DESCRIPTION

Aspects and advantages of the technology will be set forth in part in the following description, or may be obvious from the description, or may be learned through practice of the technology.

In one aspect, the present subject matter is directed to a system for monitoring soil conditions within a field. The system may include an agricultural implement configured to be traversed across a field. The implement may include a frame extending laterally between a first side and a second side. The implement may further include a plurality of ground engaging tools pivotally coupled to the frame. The ground engaging tools may be spaced apart from one another laterally between the first and second sides of the frame. The implement may further include a plurality of biasing elements. Each biasing element may be coupled between the frame and a corresponding ground engaging tool of the plurality of ground engaging tools and be configured bias the corresponding ground engaging tool to a predetermined ground engaging tool position relative to the frame. The system may also include a plurality of sensors. Each sensor may be configured to detect a parameter indicative of a current position of one of the plurality of ground engaging tools relative to the predetermined ground engaging tool position. Additionally, the system may include a controller communicatively coupled to the plurality of sensors. The controller may be configured to monitor a displacement of each ground engaging tool relative to the predetermined ground engaging tool position based on sensor measurements provided by the plurality of sensors. The controller may also be configured to determine a current global ground engaging tool displacement parameter for the implement based on the monitored displacements of the plurality of ground engaging tools. Additionally, the controller may be configured to identify a soil condition for a swath of the field being traversed by the implement based on a comparison between the current global ground engaging tool displacement parameter and a predetermined global displacement threshold.

In another aspect, the present subject matter is directed to a method for monitoring soil conditions within a field during operation of an agricultural implement. The implement may include a frame extending laterally between a first side and a second side. The implement may further include a plurality of ground engaging tools pivotally coupled to the frame. The ground engaging tools may be spaced apart from one another laterally between the first and second sides of the frame. The implement may further include a plurality of biasing elements. Each biasing element may be coupled between the frame and a corresponding ground engaging tool of the plurality of ground engaging tools and is configured bias the corresponding ground engaging tool to a predetermined ground engaging tool position relative to the frame. The method may include receiving, with a computing device, data indicative of a current position of each of the plurality of ground engaging tools relative to a predetermined ground engaging tool position. The method may also include determining, with the computing device, a current global ground engaging tool displacement parameter for the implement based on the displacements of the plurality of ground engaging tools. Additionally, the method may include identifying, with the computing device, a soil condition for a swath of the field being traversed by the implement based on a comparison between the current global ground engaging tool displacement parameter and a predetermined global displacement threshold.

These and other features, aspects and advantages of the present technology will become better understood with reference to the following description and appended claims. The accompanying drawings, which are incorporated in and constitute a part of this specification, illustrate embodiments of the technology and, together with the description, serve to explain the principles of the technology.

BRIEF DESCRIPTION OF THE DRAWINGS

A full and enabling disclosure of the present technology, including the best mode thereof, directed to one of ordinary skill in the art, is set forth in the specification, which makes reference to the appended figures, in which.

Figure 1:
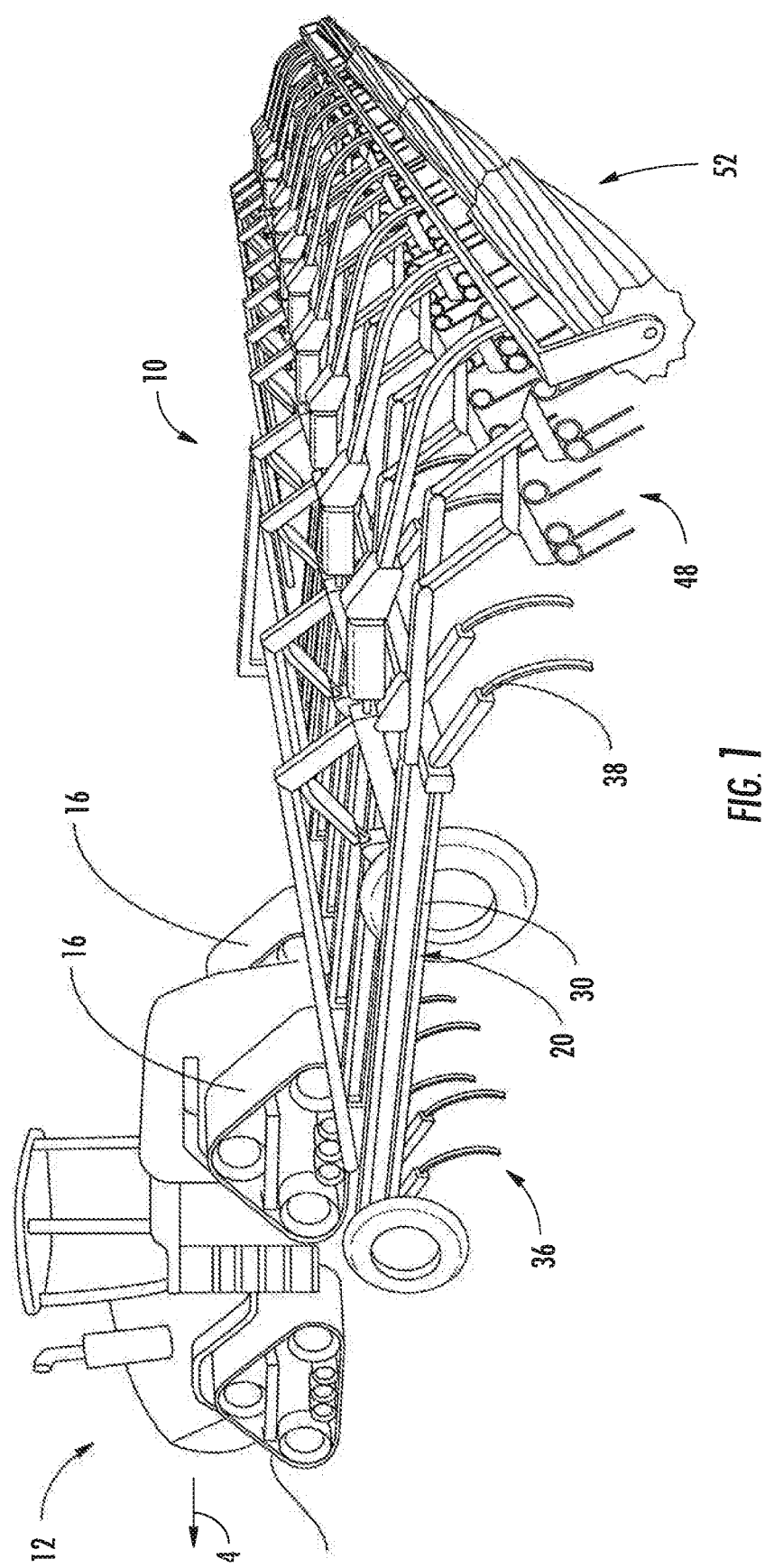
FIG. 1 illustrates a perspective view of one embodiment of an agricultural implement coupled to a work vehicle in accordance with aspects of the present subject matter.

Repeat use of reference characters in the present specification and drawings is intended to represent the same or analogous features or elements of the present technology.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to systems and methods for monitoring the operation of one or more ground engaging tools of an agricultural implement. In several embodiments, the disclosed system and method may monitor the position of the one or more ground engaging tools and determine various conditions associated with the operation of the ground engaging tools based on the monitored positions thereof. For example, the various conditions may be associated with a single ground engaging tool, such as the occurrence of a ground engaging tool float event with respect to that particular ground engaging tool, or associated with a plurality of the ground engaging tools, such as a soil condition of a swath of field being traversed by the implement.

In accordance with aspects of the present subject matter, the disclosed system and method may detect the occurrence of ground engaging tool float events for particular ground engaging tools of the agricultural implement. Specifically, in several embodiments, a controller may monitor a current position of a ground engaging tool of the implement relative to an implement frame and identify a time period across which the ground engaging tool is displaced from a predetermined ground engaging tool position. For instance, the ground engaging tool may be displaced from the predetermined ground engaging tool position due to the presence of firm or compacted soil or due to the speed at which the implement is being towed by a work vehicle. Upon identifying the time period, a controller may be configured to compare such time period to a threshold time period to determine when a ground engaging tool float event is occurring during operation of the implement.

Furthermore, the disclosed system and method may monitor the soil conditions within a swath of a field being traversed by the implement. Specifically, in several embodiments, a controller may be configured to monitor the displacement of a plurality of ground engaging tools of an implement. For instance, each ground engaging tool may experience varying soil conditions, which may result in differing ground engaging tool displacements. The controller may be configured to determine a current global ground engaging tool displacement parameter for the implement based on the monitored ground engaging tool displacements of the various ground engaging tools. Using the current global ground engaging tool displacement parameter, the controller may be configured to identify a soil condition for a portion of the field currently being traversed by the implement.

Figure 2:
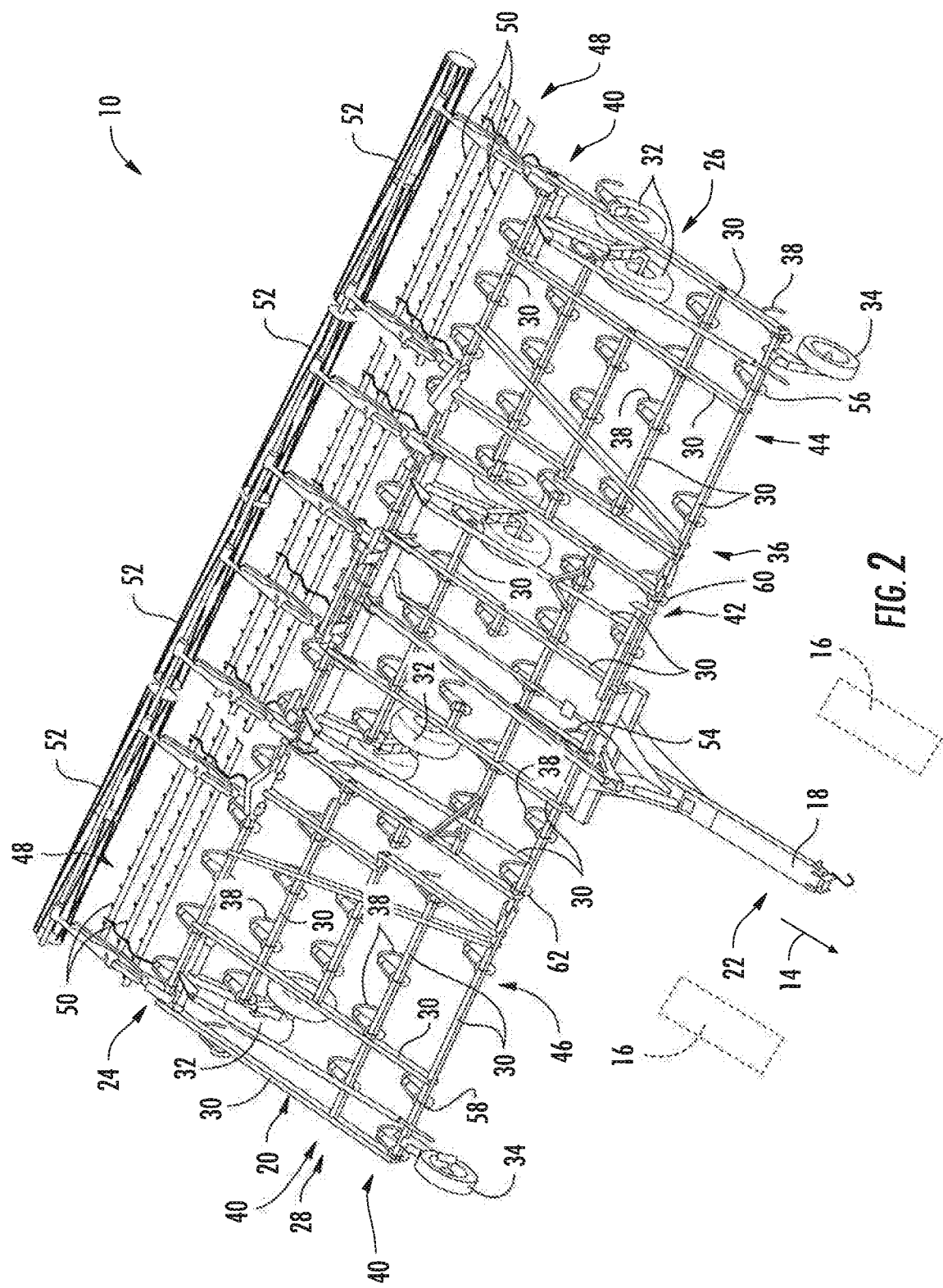
FIG. 2 illustrates an alternative perspective view of an agricultural implement in accordance with aspects of the present subject matter, particularly illustrating various components of the implement.

Referring now to the drawings, FIGS. 1 and 2 illustrate differing perspective views of one embodiment of an agricultural implement 10 in accordance with aspects of the present subject matter. Specifically, FIG. 1 illustrates a perspective view of the agricultural implement 10 coupled to a work vehicle 12. Additionally, FIG. 2 illustrates a perspective view of the implement 10, particularly illustrating various components of the implement 10.

In general, the implement 10 may be configured to be towed across a field along a direction of travel 14 by the work vehicle 12. As shown, the work vehicle 12 may be configured as an agricultural tractor having a plurality of track assemblies 16 for use in traversing the field. It should be appreciated, however, that the work vehicle 12 may be configured as any suitable work vehicle, such as a wheeled vehicle. The implement 10 may be coupled to the work vehicle 12 via a hitch assembly 18 or using any other suitable attachment means. For example, the hitch assembly 18 may couple to an implement frame 20.

The implement 10 may include the implement frame 20. As shown, the frame 20 may extend longitudinally between a forward end 22 and an aft end 24. The frame 20 may also extend laterally between a first side 26 and a second side 28. In this respect, the frame 16 generally includes a plurality of structural frame members 30, such as beams, bars, and/or the like, configured to support or couple to a plurality of components. Additionally, a plurality of wheels may be coupled to the frame 20, such as a set of centrally located wheels 32 and a set of front pivoting wheels 34, to facilitate towing the implement 10 in the direction of travel 14.

In one embodiment, the frame 20 may be configured to support a cultivator 36, which may be configured to till or otherwise break the soil over which the implement 10 travels to create a seedbed. In this respect, the cultivator 36 may include a plurality of ground engaging tools 38, which are pulled through the soil as the implement 10 moves across the field in the direction of travel 14. As will be discussed in greater detail below, the ground engaging tools 38 may be configured to be pivotally mounted to the frame 20 to allow the ground engaging tools 38 pivot out of the way of rocks or other impediments in the soil. As shown, the ground engaging tools 38 may be arranged into a plurality of ranks 40, which are spaced apart from one another longitudinally between the forward end 22 and the aft end 24 of the frame 20.

In several embodiments, the frame 20 may include one or more sections. As illustrated in FIG. 2, for example, the frame 20 may include a main section 42 positioned centrally between the first and second sides 26, 28 of the frame 20. The frame 20 may also include a first wing section 44 positioned proximate to the first side 26 of the frame 20. Similarly, the frame 20 may also include a second wing section 46 positioned proximate to the second side 28 of the frame 20. The first and second wing sections 44, 46 may be pivotally coupled to the main section 42 of the frame 20. In this respect, the first and second wing sections 44, 46 may be configured to fold up relative to the main section 42 to reduce the lateral width of the implement 10 to permit, for example, storage or transportation of the implement on a road. In should be appreciated that the frame 20 may include any suitable number of wing sections.

Moreover, as shown in FIGS. 1 and 2, the implement 10 may also include one or more harrows 48. As is generally understood, the harrows 48 may be configured to be pivotally coupled to the frame 20. The harrows 48 may include a plurality of ground engaging elements 50, such as tines or spikes, which are configured to level or otherwise flatten any windrows or ridges in the soil created by the cultivator 36. Specifically, the ground engaging elements 50 may be configured to be pulled through the soil as the implement 10 moves across the field in the direction of travel 14. It should be appreciated that the implement 10 may include any suitable number of harrows 48. In fact, some embodiments of the implement 10 may not include any harrows 48.

Moreover, in one embodiment, the implement 10 may optionally include one or more baskets or rotary firming wheels 52. As is generally understood, the baskets 52 may be configured to reduce the number of clods in the soil and/or firm the soil over which the implement 10 travels. As shown, each basket 52 may be configured to be pivotally coupled to one of the harrows 48. Alternately, the baskets 52 may be configured to be pivotally coupled to the frame 20 or any other suitable location of the implement 10. It should be appreciated that the implement 10 may include any suitable number of baskets 52. In fact, some embodiments of the implement 10 may not include any baskets 52.

It should be appreciated that the configuration of the implement 10 described above and shown in FIGS. 1 and 2 is provided only to place the present subject matter in an exemplary field of use. Thus, it should be appreciated that the present subject matter may be readily adaptable to any manner of implement configuration.

Figure 3:
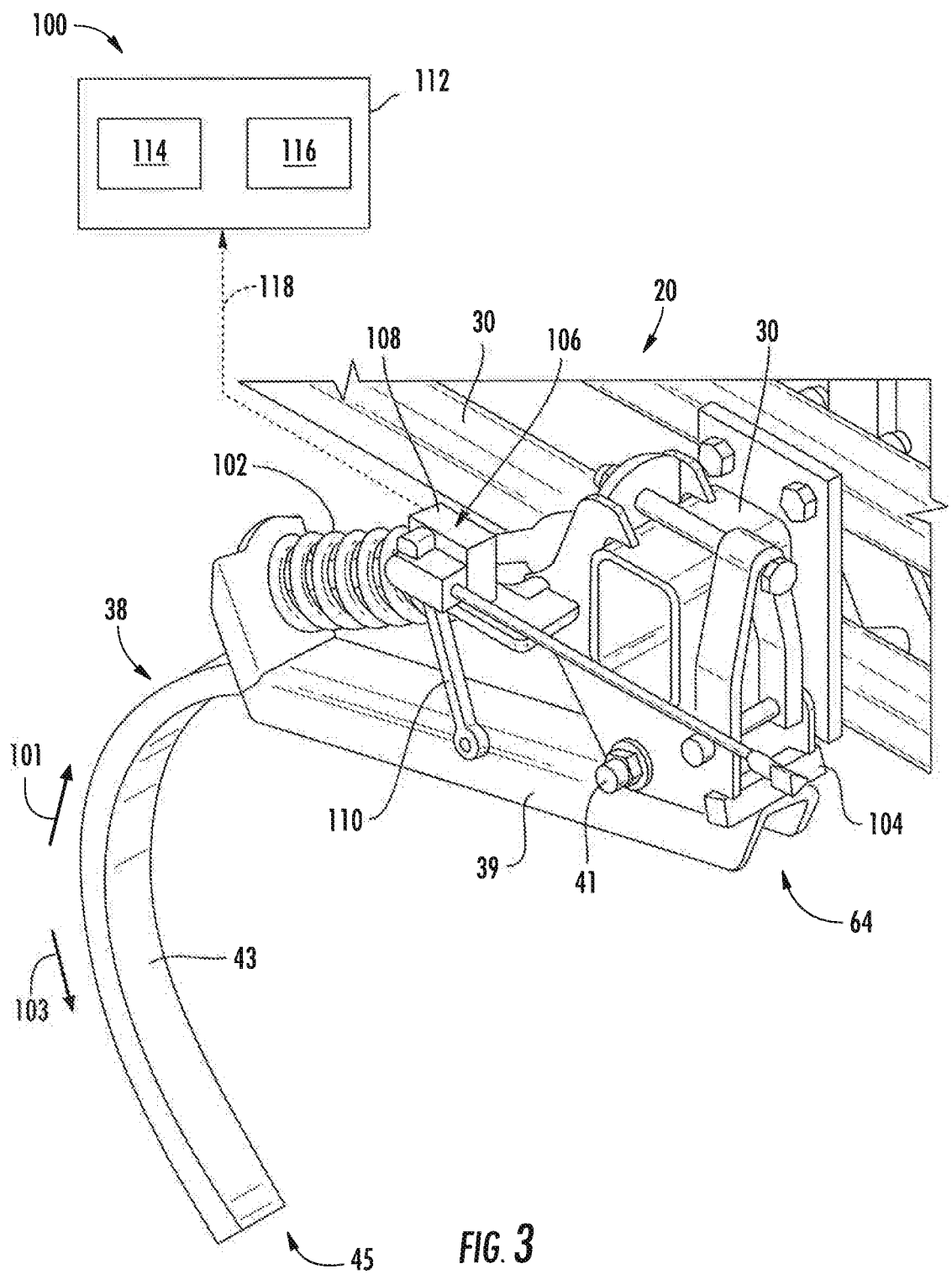
FIG. 3 illustrates a perspective view of one embodiment of a system for detecting ground engaging tool float for an agricultural implement in accordance with aspects of the present subject matter, particularly illustrating the system including a sensor for detecting a parameter indicative of a current position of a ground engaging tool relative to a frame.

Referring now to FIG. 3, a side view of one embodiment of a system 100 for detecting ground engaging tool float for an agricultural implement is illustrated in accordance with aspects of the present subject matter. In general, the system 100 will be described herein with reference to the implement 10 and one of the ground engaging tools 38 described above with reference to FIGS. 1-2. However, it should be appreciated by those of ordinary skill in the art that the disclosed system 100 may generally be utilized with ground engaging tools having any other suitable ground engaging tool configuration and/or implements having any other suitable implement configuration.

As shown in FIG. 3, the system 100 may include a ground engaging tool 38 pivotally coupled to the implement frame 20. More specifically, the ground engaging tool 38 may generally include a shank portion 39 configured to be pivotally coupled to the frame 20 (e.g., at pivot point 41) and a ground-engaging portion 43 extending from the shank portion 39 along a curved or arcuate profile. As shown in FIG. 3, the ground-engaging portion 43 may include a tip end 45 that is configured to penetrate into or otherwise engage the ground as the implement 10 is being pulled through the field. In one embodiment, the ground engaging tool 38 may be configured as a chisel. However, one of ordinary skill in the art would appreciate that the ground engaging tool 38 may be configured as a sweep, tine, or any other suitable ground engaging tool.

The system 100 may also include a biasing element 102 coupled between the frame 20 and the ground engaging tool 38. In this respect, the biasing element 102 may be configured to bias the ground engaging tool 38 to a predetermined ground engaging tool position (e.g., a home or base position) relative to the frame 20. In general, the predetermined ground engaging tool position may correspond to a ground engaging tool position in which the ground engaging tool 38 penetrates the soil to a desired depth. In several embodiments, the predetermined ground engaging tool position may be set by a mechanical stop 104. In operation, the biasing element 102 may permit relative movement between the ground engaging tool 36 and the frame 20. For example, the biasing element 102 may be configured to bias the ground engaging tool 38 to pivot relative to the frame 20 in a first pivot direction (e.g., as indicated by arrow 103 in FIG. 3) until an end 64 of the shank portion 39 of the ground engaging tool 38 contacts the stop 104. The biasing element 102 may also allow the ground engaging tool 38 to pivot away from the predetermined ground engaging tool position (e.g., to a shallower depth of penetration), such as in a second pivot direction (e.g., as indicated by arrow 101 in FIG. 3) opposite the first pivot direction 101, when encountering rocks or other impediments in the field. As shown in FIG. 3, the biasing element 102 may be configured as a spring. As will be discussed, however, the biasing element 102 may be configured as an actuator or any other suitable biasing element.

In accordance with aspects of the present subject matter, the system 100 may also include a sensor 106 provided in operative association with the ground engaging tool 38 or the biasing element 102. In general, the sensor 106 may be configured to detect an operating parameter indicative of a current position of the ground engaging tool 38 relative to the frame 20. In several embodiments, the sensor 106 may generally correspond to any suitable sensor(s) or sensing device(s) that is configured to directly or indirectly detect the pivotal motion of the ground engaging tool 38. For example, the sensor 106 may be configured as a rotary sensor 108 (e.g., a rotary potentiometer or a magnetic rotary sensor) coupled to one of the frame 20 or the ground engaging tool 38 and an associated sensor linkage 110 coupled between the rotary sensor 108 and the other adjacent component. For instance, as shown in the illustrated embodiment, the rotary sensor 108 is coupled to a portion of the frame 20, with the sensor linkage 110 being coupled between the rotary sensor 108 and the ground engaging tool 38. As such, when the ground engaging tool 38 pivots relative to the frame 20, the motion of the ground engaging tool 38 may be detected by the rotary sensor 108 via the mechanical linkage provided by the sensor linkage 110.

In other embodiments, the sensor 106 may correspond to any other suitable sensor(s) or sensing device(s) configured to detect the pivotal motion of the ground engaging tool 38. For instance, the sensor 106 may correspond to a linear potentiometer, a proximity sensor, and/or any other suitable transducer (e.g., ultrasonic, electromagnetic, infrared, etc.) that allows the pivotal motion of the ground engaging tool 38 relative to the frame 20 to be directly or indirectly detected.

As indicated above, FIG. 3 simply illustrates a single ground engaging tool 38 of the implement 10, with the biasing element 102 being coupled between the frame 20 and the illustrated ground engaging tool 38 and the sensor 106 being provided to monitor the displacement or pivotal motion of such ground engaging tool 38. However, a person of ordinary skill in the art will appreciate that any or all of the remaining ground engaging tools 38 of the disclosed implement 10 may similarly be provide in operative association with a corresponding biasing element 102 and an associated sensor 106. For example, as will be described below with reference to FIG. 8, a biasing element 102 may be coupled to each of a plurality of ground engaging tools of the implement 10, such as ground engaging tools 54, 56, 58, 60, 62. Moreover, in such an embodiment, a corresponding sensor 106 may be provided in operative association with each ground engaging tool 54, 56, 58, 60, 62 and/or its associated biasing element 102.

Referring still to FIG. 3, the system 100 may further include a controller 112 configured to electronically control the operation of one or more components of the implement 10 or the work vehicle 12. In general, the controller 112 may comprise any suitable processor-based device known in the art, such as a computing device or any suitable combination of computing devices. Thus, in several embodiments, the controller 112 may include one or more processor(s) 114 and associated memory device(s) 116 configured to perform a variety of computer-implemented functions. As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 116 of the controller 112 may generally comprise memory element(s) including, but not limited to, a computer readable medium (e.g., random access memory (RAM)), a computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 116 may generally be configured to store suitable computer-readable instructions that, when implemented by the processor(s) 114, configure the controller 112 to perform various computer-implemented functions, such as one or more aspects of the methods 200 and 400 described below with reference to FIGS. 7 and 9. In addition, the controller 112 may also include various other suitable components, such as a communications circuit or module, one or more input/output channels, a data/control bus and/or the like.

It should be appreciated that the controller 112 may correspond to an existing controller of the implement 10 or the work vehicle 12 or the controller 112 may correspond to a separate processing device. For instance, in one embodiment, the controller 112 may form all or part of a separate plug-in module that may be installed within the implement 10 or the work vehicle 12 to allow for the disclosed system and method to be implemented without requiring additional software to be uploaded onto existing control devices of the implement 10 or the work vehicle 12.

In several embodiments, the controller 112 may be configured to monitor a current position of the ground engaging tool 38 relative to the frame 20. Specifically, the controller 112 may be communicatively coupled to the sensor 106, such as the rotary sensor 108, via a wired or wireless connection to allow measurement signals (e.g., indicated by dashed line 118 in FIG. 3) to be transmitted from the sensor 106 to the controller 112. The controller 112 may then be configured determine or estimate the current position of the ground engaging tool 38 relative to the frame 20 based on the measurement signals 118 received from the sensor 106. For instance, the controller 112 may include a look-up table or suitable mathematical formula stored within its memory 116 that correlates the sensor measurements to the current position of the ground engaging tool 38.

By monitoring the current position of the ground engaging tool 38 relative to the frame 20, the controller 112 may also be configured to determine when a ground engaging tool float event is occurring during operation of the implement 10. For instance, the controller 112 may be configured to determine when the ground engaging tool 38 is displaced from the predetermined ground engaging tool position by comparing the current position of the ground engaging tool 38 to the predetermined ground engaging tool position. Thereafter, in the event that the ground engaging tool 38 is displaced from the predetermined ground engaging tool position, the controller 112 may be configured identify a time period across which the ground engaging tool 38 is displaced from the predetermined ground engaging tool position. In such instance, the controller 112 may compare the identified time period that the ground engaging tool 38 is displaced from the predetermined ground engaging tool position to a threshold time period associated with the occurrence of ground engaging tool float events. When the identified time period exceeds the threshold time period, the controller 112 may be configured to determine that a ground engaging tool float event has occurred.

Figure 4:
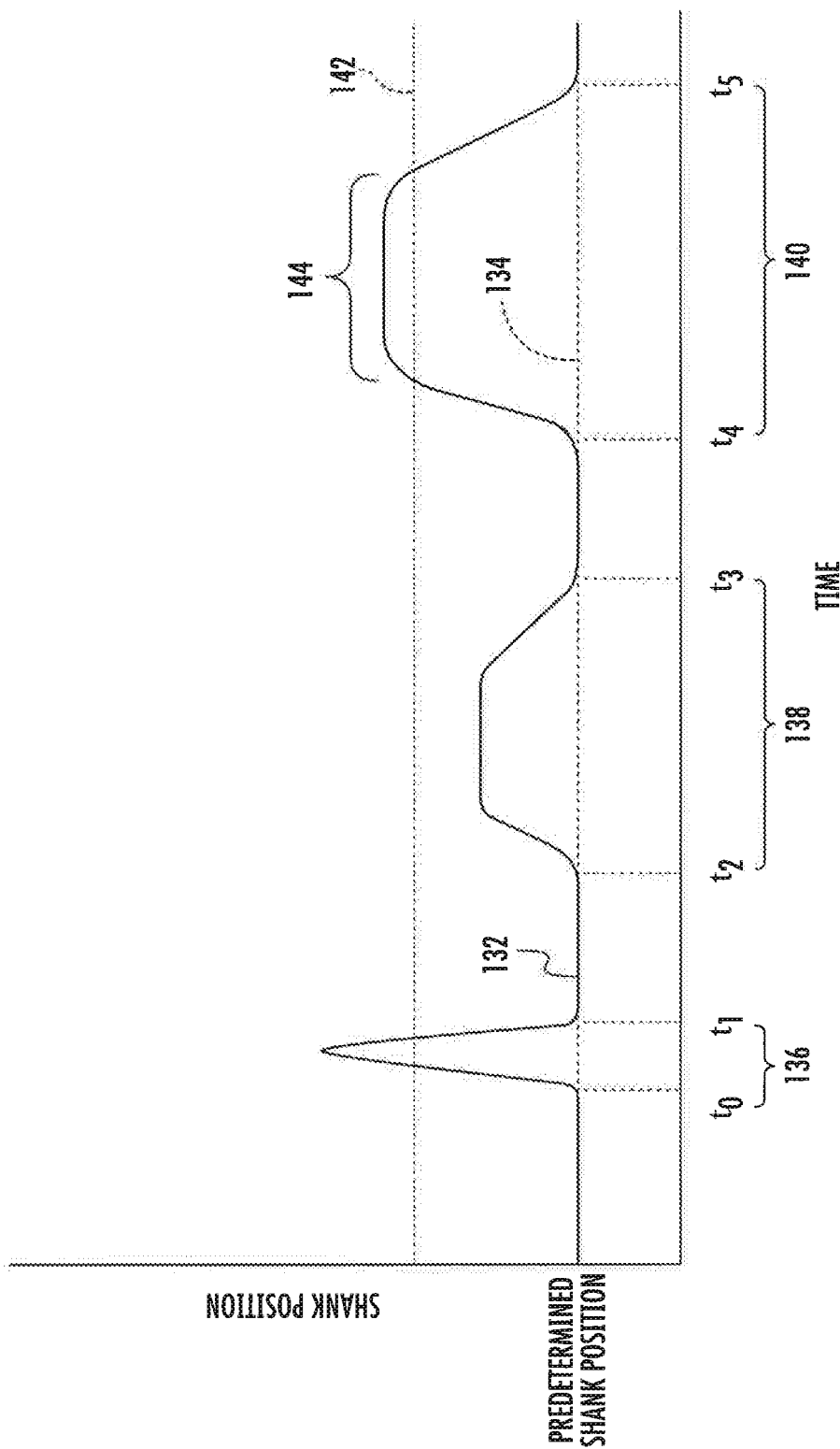
FIG. 4 illustrates a graphical view of an example dataset charting the displacement of a ground engaging tool relative a predetermined ground engaging tool position over time in accordance with aspects of the present subject matter.

For instance, FIG. 4 illustrates a graphical view of an example dataset charting the displacement of one of the ground engaging tools 38 of the implement 10 (e.g., as indicated by solid line 132) relative the predetermined ground engaging tool position (e.g., as indicated by dashed line 134) over time as monitored by the controller 112. As shown in FIG. 4, during various different time periods, the ground engaging tool 38 is displaced from its predetermined ground engaging tool position 134, such as at a first time period 136 between time to and time $t_1$, a second time period 138 between time $t_2$ and time $t_3$, and a third time period 140 between time $t_4$ and $t_5$. In such instances, the controller 112 may be configured to identify the length of each time period and compare it to a given threshold time period. In the event that the length of any of such time periods exceeds the threshold time period, the controller 112 may determine that a float event has occurred. For instance, in the example dataset of FIG. 4, it may be assumed that the first time period 136 is less than the threshold time period while the second and third time periods 138, 140 exceed the threshold time period. In such instance, the ground engaging tool displacement occurring across the first time period 136 may be indicative of a short, non-float displacement event, such as a ground engaging tool trip event occurring when the ground engaging tool 38 contacts a rock with the field and quickly pivots away from and back to the predetermined ground engaging tool position 132. In contrast, the ground engaging tool displacement occurring across second and third time periods 138, 140 may be indicative of more prolonged displacement event, such as when the ground engaging tool floats away from the predetermined ground engaging tool position 132 for an extended period of time due to compacted or hardened soil conditions.

It should be appreciated that the time period threshold utilized by the controller 112 may generally be selected so as to prevent instantaneous or significantly short displacement events from being classified as float events (e.g., ground engaging tool trip events occurring due to random contact with rocks or other impediments within the soil). For instance, in one embodiment, the time period threshold may be greater than about 0.1 seconds, such as greater than about 0.5 seconds or greater than about 1 second or greater than about 2 seconds.

Furthermore, in addition to utilizing a time-based threshold, the controller 112 may also be configured to identify when a ground engaging tool float event has occurred based at least partially on a magnitude of the displacement of the ground engaging tool 38 during operation of the implement 10. More specifically, the controller 112 may be configured to monitor the magnitude of the displacement of the ground engaging tool 38 relative to the predetermined ground engaging tool position. For instance, the controller 112 may be configured to determine the magnitude of the displacement of the ground engaging tool 38 relative to the predetermined ground engaging tool position by comparing the current position of the ground engaging tool 38 to the predetermined ground engaging tool position. Once the displacement of the ground engaging tool 38 is determined, the controller 112 may be configured to compare the determined displacement to a threshold displacement value (e.g., as indicated by line 142 in FIG. 4). Thereafter, in the event that the determined displacement of the ground engaging tool 38 exceeds the threshold displacement value, the controller 112 may be configured to identify the time period across which the displacement of the ground engaging tool 38 exceeds the threshold displacement value and compare the identified time period to the threshold time period. When the identified time period exceeds the threshold time period, the controller 112 may be configured to determine that the ground engaging tool float event has occurred.

For instance, using the example dataset shown in FIG. 4, the controller 112 may only classify a portion of the third time period 140 as a float event. Specifically, even though the second time period 138 may correspond to a time period that exceeds the time period threshold, the magnitude of the ground engaging tool displacement never exceeds the threshold displacement value 142. In contrast, during the third time period 140, the ground engaging tool displacement exceeds the threshold displacement value 142 for a given period of time 144. Assuming such time period 144 exceeds the time period threshold, the controller 112 may identify such ground engaging tool displacement as corresponding to a float event.

Referring back to FIG. 3, in several embodiments, when it is determined that a ground engaging tool float is occurring, the controller 112 may be configured to initiate a control action associated with reducing the displacement defined between the current position of the ground engaging tool 38 and the predetermined ground engaging tool position. For instance, in one embodiment, the controller 112 may be configured to transmit a notification to the operator of the implement 10 (e.g., by causing a visual or audible notification or indicator to be presented to the operator within the work vehicle 12) that provides an indication that ground engaging tool float is occurring. In such instances, the operator may then choose to initiate any suitable corrective action he/she believes is necessary, such as by reducing the ground speed of the implement 10 and/or the work vehicle 12. Alternatively, the controller 112 may be configured to automatically control the operation of one or more components of the implement 10 and/or the work vehicle 12 (e.g., the vehicle's engine or transmission) in a manner that reduces the ground speed of the implement 10 and/or the work vehicle 12 when ground engaging tool float occurs, such as by reducing or limiting the engine power output. In even further embodiments, the controller 112 may be configured to initiate any other suitable control action. For instance, as will be described below with reference to FIG. 6, the controller 112 may be configured to automatically adjust the down pressure exerted on the ground engaging tool 38 by the biasing element 102 so as to reduce the displacement defined between the current position of the ground engaging tool 38 and the predetermined ground engaging tool position.

Figure 5:
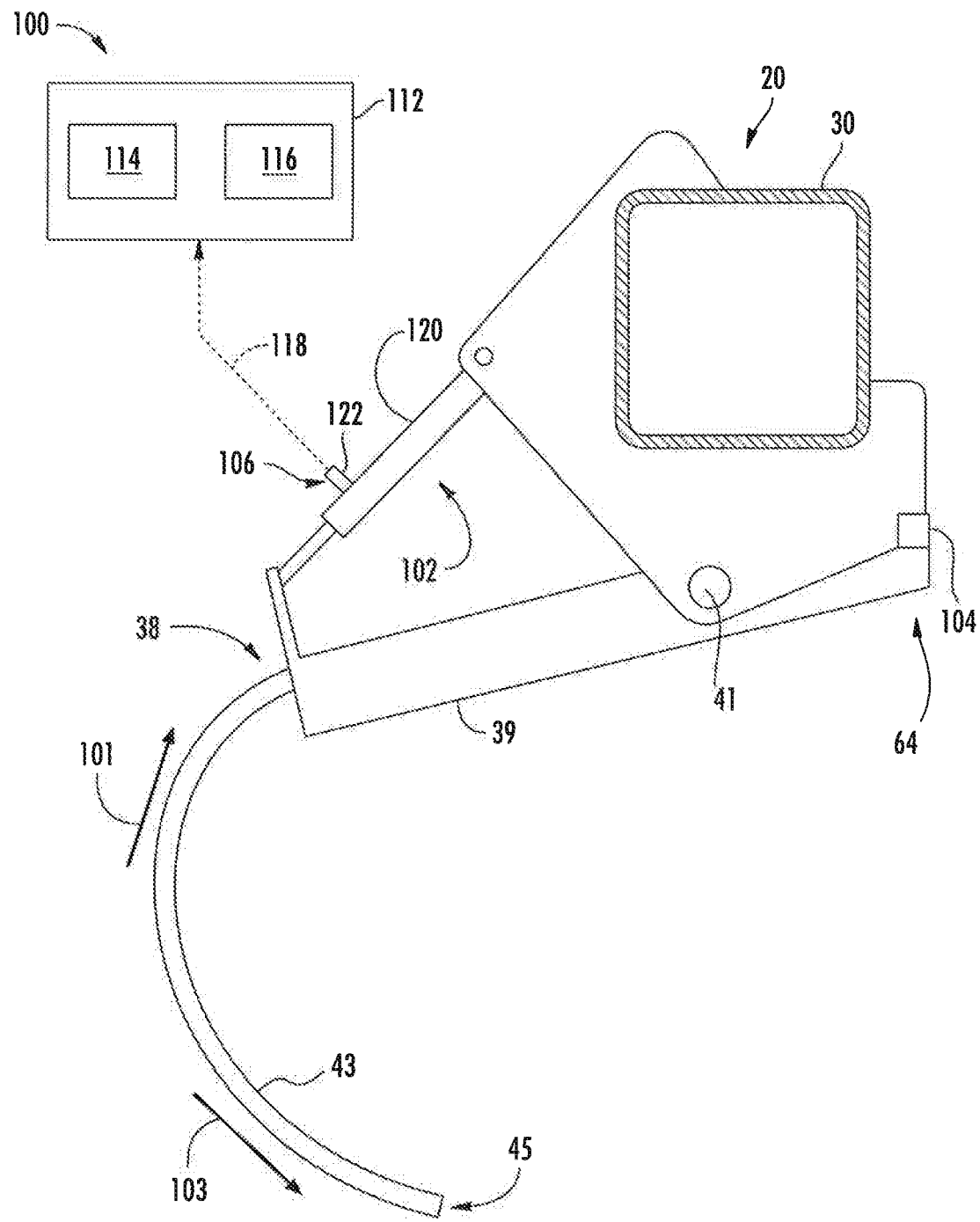
FIG. 5 illustrates a perspective view of another embodiment of a system for detecting ground engaging tool float for an agricultural implement in accordance with aspects of the present subject matter, particularly illustrating the system including a fluid-driven actuator for adjusting a down pressure exerted on a ground engaging tool.

Referring now to FIG. 5, a side view of another embodiment of the system 100 described above with reference to FIG. 3 is illustrated in accordance with aspects of the present subject matter. As shown, the system 100 may generally be configured the same as or similar to that described above with reference to FIG. 3. For instance, the system 100 may include a biasing element 102 coupled between the frame 20 and the ground engaging tool 38, with the biasing element 102 being configured to bias the ground engaging tool 38 to a predetermined ground engaging tool position relative to the frame 20. However, as shown in FIG. 5, unlike the above-described embodiment, the biasing element 102 may be configured as a fluid-driven actuator 120, such as hydraulic actuator and/or a pneumatic actuator. Specifically, in one embodiment, the actuator 120 may be configured to adjust a down pressure exerted on the ground engaging tool 38 based on a fluid pressure associated with the fluid-driven actuator. It should be appreciated that, in alternate embodiments, the biasing element 102 may be a solenoid, a linear actuator, or any other suitable type of actuator.

Similar to the embodiment described above with reference to FIG. 3, the system 100 may include a sensor 106 configured to monitor an operating parameter indicative of a current position of the ground engaging tool 38 relative to the frame 20. However, as shown in FIG. 5, unlike the above-described embodiment, the sensor 106 may be configured as a pressure sensor 122 provided in operative association with the fluid-driven actuator 120. In general, the pressure sensor 122 may be configured to detect or measure a pressure of a fluid supplied within the actuator 120. For example, in one embodiment, the pressure sensor 122 may be provided in fluid communication with a fluid chamber defined within the actuator 120 (e.g., a piston-side chamber or a rod-side chamber of the actuator 120). Alternatively, the pressure sensor 122 may be installed at any other suitable location that allows the pressure sensor 122 to measure the pressure of the fluid supplied within the actuator 120, such as by installing the pressure sensor 122 in fluid communication with a hose or conduit configured to supply fluid to the actuator 120. The pressure of the fluid supplied within the actuator 120 may, in turn, be indicative of the current position of the ground engaging tool 38 relative to the frame 20. In this respect, the controller 112 may include a look-up table or suitable mathematical formula stored within its memory 116 that correlates the pressure measurements to the current position of the ground engaging tool 38.

Figure 6:
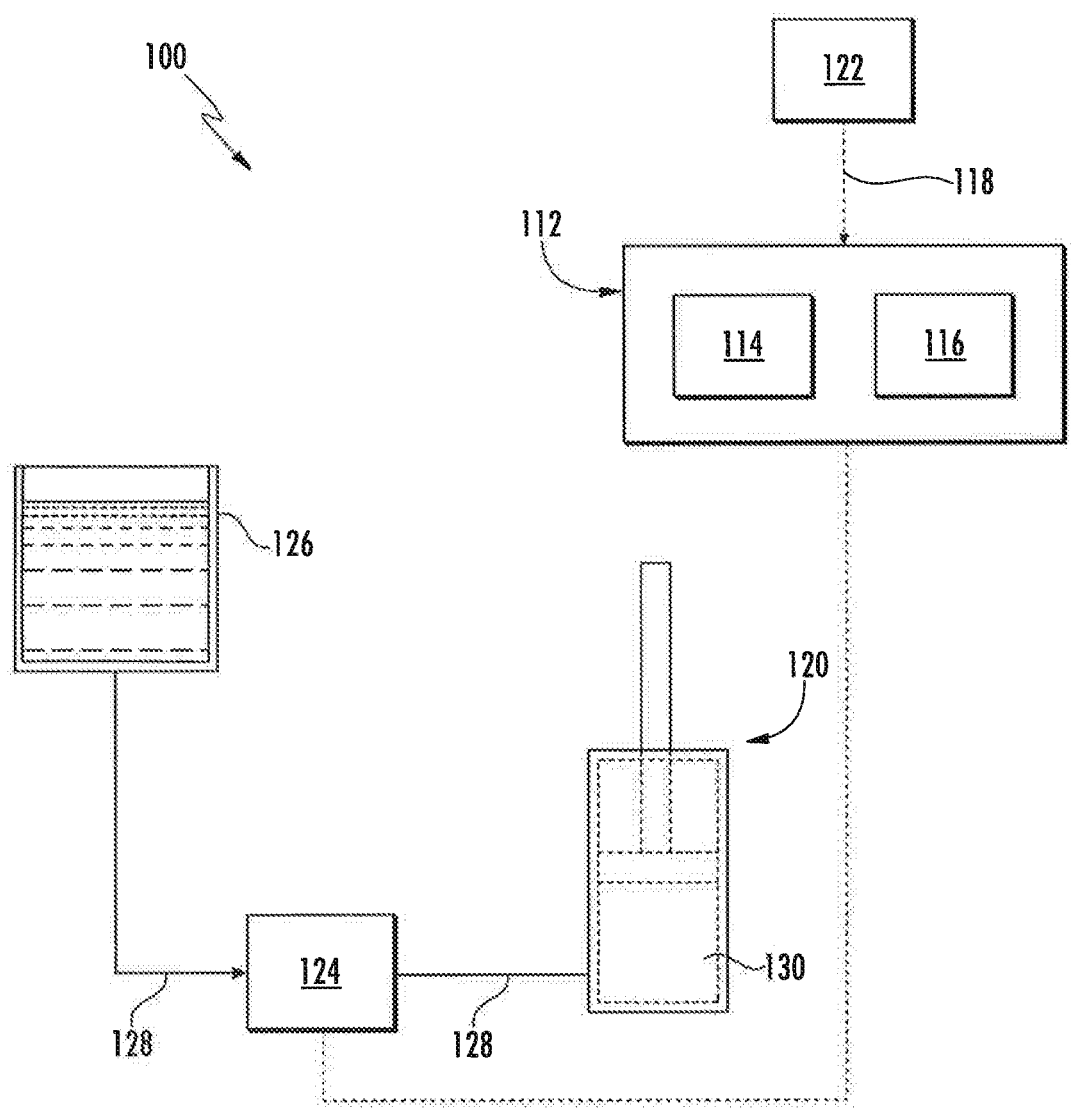
FIG. 6 illustrates a schematic view of another embodiment of a system for detecting ground engaging tool float for an agricultural implement in accordance with aspects of the present subject matter.

Referring now to FIG. 6, a schematic diagram of a specific implementation of the system 100 described above with reference to FIG. 5 is illustrated in accordance with aspects of the present subject matter. It should be appreciated that, in the illustrated embodiment, the actuator 120 corresponds to a hydraulic cylinder. However, as indicated above, the actuator 120 also correspond to any other suitable fluid-driven actuator, such as a pneumatic actuator.

As shown in FIG. 6, the controller 112 may, in several embodiments, be configured to be coupled to suitable components for automatically controlling the operation of the actuator 120, thereby allowing the controller 112 to actively adjust the adjust the down pressure exerted on the ground engaging tool 38. For example, in the illustrated embodiment, the controller 112 may be communicatively coupled to a suitable pressure regulating valve 124 (PRV) (e.g., a solenoid-activated valve) configured to regulate the pressure of hydraulic fluid supplied to the actuator 120 (e.g., from a hydraulic fluid tank 126 or pump of the implement 10 or the work vehicle 12 via one or more fluid conduits 128). Specifically, as shown schematically in FIG. 5, the controller 112 may be coupled to the PRV 124 so as to regulate the pressure of the hydraulic fluid supplied to a cap or piston end 130 of the actuator 120 (e.g., via one or more conduits 128). In such an embodiment, the pressure of the fluid supplied from the PRV 124 may be directly proportional to the pressure supplied at the piston end 130 of the actuator 120, thereby allowing the controller 112 to control the displacement of the actuator 120. It should be appreciated that, although FIG. 6 only illustrates the controller 112 coupled to a single PRV for controlling the operation of the actuator 120 for one of the ground engaging tools 38, similar hydraulic components may be utilized to control the corresponding actuators 120 associated with the remaining ground engaging tools 38 of the implement 10.

Utilizing the system configuration shown in FIG. 6, the controller 112 may be configured to automatically control the operation of the actuator 120 so as to increase the down pressure on the ground engaging tool 38. Specifically, as indicated above, the controller 112 may be configured to detect the occurrence of ground engaging tool float with respect to the displacement of the ground engaging tool 38. When a ground engaging tool float is occurring, the controller 112 may be configured to electronically control operation of the PRV 124 to adjust the fluid pressure supplied within the actuator 120. For instance, the controller 112 may be configured to control the operation of the PRV 124 such that the fluid pressure supplied to the actuator 120 is increased when it is detected that a ground engaging tool float is occurring. Increasing the fluid pressure within the actuator 120 may increase the down pressure on the ground engaging tool 38, which, in turn, may reduce the displacement defined between the current position of the ground engaging tool 38 and the predetermined ground engaging tool position.

Although the sensor 106 is described above as being configured as a rotary sensor 108 (FIG. 3) or a pressure sensor 120 (FIG. 5), a person of ordinary skill in the art would appreciate that the sensor 108 may be any suitable sensor(s) or sensing device(s) configured to detect an operating parameter indicative of the current position of the ground engaging tool 38 relative to the frame 20. For example, the sensor 106 may be configured as an accelerometer coupled to the ground engaging tool 38. As such, when the ground engaging tool 38 pivots relative to the frame 20, the acceleration of the ground engaging tool 38 relative to the frame 20 may be detected by the accelerometer. The acceleration of the ground engaging tool 38 may, in turn, be indicative of the current position of the ground engaging tool 38 relative to the frame 20. For example, the controller 112 may be configured to determine the current position of the ground engaging tool 38 based on a duration of the detected acceleration. In this respect, the controller 112 may include a look-up table or suitable mathematical formula stored within its memory 116 that correlates the acceleration measurements to the current position of the ground engaging tool 38.

Figure 7:
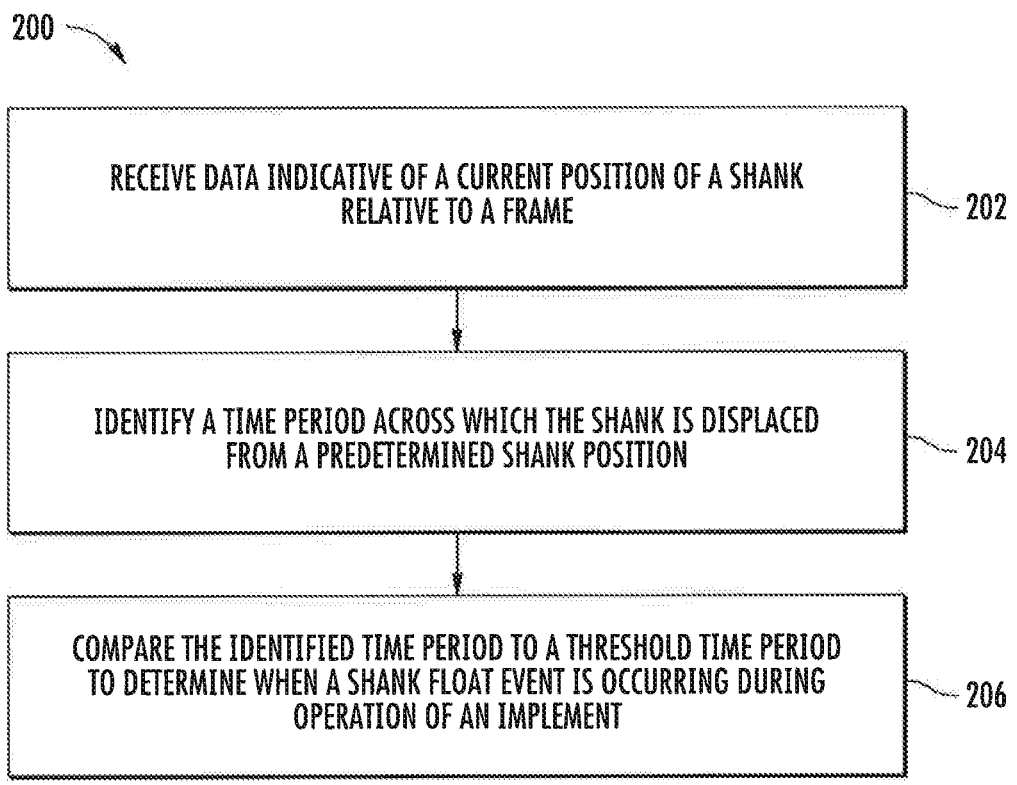
FIG. 7 illustrates a flow diagram of one embodiment of a method for detecting ground engaging tool float for an agricultural implement in accordance with aspects of the present subject matter.

Referring now to FIG. 7, a flow diagram of one embodiment of a method 200 for detecting ground engaging tool float for an agricultural implement is illustrated in accordance with aspects of the present subject matter. In general, the method 200 will be described herein with reference to the implement 10, the ground engaging tools 38, and the system 100 described above with reference to FIGS. 1-6. However, it should be appreciated by those of ordinary skill in the art that the disclosed method 200 may generally be utilized to detect ground engaging tool float for any agricultural implement having any suitable implement configuration and/or of any ground engaging tool having any suitable ground engaging tool configuration. In addition, although FIG. 7 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 7, at (202), the method 200 may include receiving data indicative of a current position of a ground engaging tool relative to a frame of an agricultural implement. For instance, as indicated above, the controller 112 may be communicatively coupled to a sensor 106 configured to monitor an operating parameter indicative of the current position of the ground engaging tool 38 relative to the frame 20. As such, measurement signals or sensor data 118 transmitted from the sensor 106 may be received by the controller 112 for monitoring the current position and/or displacement of the ground engaging tool 38.

Additionally, at (204), the method 200 may include identifying a time period across which the ground engaging tool is displaced from a predetermined ground engaging tool position. Specifically, as indicated above, the controller 112 may monitor the current position of the ground engaging tool 38 relative to the predetermined ground engaging tool position so as to determine when the ground engaging tool 38 is displaced from the predetermined ground engaging tool position. The controller 112 may then identify the time period across which the ground engaging tool 38 is displaced from the predetermined ground engaging tool position.

Moreover, as shown in FIG. 6, at (206), the method 200 may include comparing the identified time period to a threshold time period to determine when a ground engaging tool float event is occurring during operation of the implement. For instance, as described above with reference to FIG. 4, the controller 112 may compare the identified time period to a corresponding threshold time period. Thereafter, assuming that the identified time period exceeds the threshold time period, the controller 112 may determine that a ground engaging tool float event has occurred across such identified time period.

Furthermore, in several embodiments, the method 200 may also include initiating a control action associated with reducing the displacement defined between the current position of the ground engaging tool and the predetermined ground engaging tool position when it is determined that a ground engaging tool float event is occurring. As indicated above, such control actions may include controlling one or more components of the implement 10 and/or the work vehicle 12. For instance, as indicated above, the controller 112 may, in one embodiment, be configured to control one or more operator-interface components located within the vehicle's cab to allow a visual and/or audible notification to be presented to the operator. In addition, or as an alternative thereto, the controller 112 may be configured to automatically initiate a control action that results in the ground speed of the implement 10 and/or the work vehicle 12 being reduced, such as by automatically controlling the operation of the vehicle's engine and/or transmission. Moreover, as described above with reference to FIG. 6, the controller 112 may also be configured to actively regulate the pressure of the fluid supplied within an associated actuator 120 (e.g., by electronically controlling the associated PRV 124) to adjust the down pressure on the ground engaging tool 38.

It should be appreciated that, in addition to detecting float events, embodiments of the system 100 described herein may also be utilized for monitoring the soil conditions within a field. Specifically, in several embodiments, the disclosed system 100 may be utilized to monitor the displacement of two or more of the ground engaging tools of an implement. For example, as indicated above, the implement 10 may include a plurality of ground engaging tools 38 spaced apart from one another laterally between the first and second sides 26, 28 of the frame 20. In such instance, each ground engaging tool 38 may experience differing magnitudes of displacement due to variations in soil conditions across the lateral width of the frame 20. For instance, the soil compacted by tracks or wheels of the work vehicle 12 towing the implement 10 may be much firmer than other areas of the field. Thus, by monitoring the individual ground engaging tool displacements of two or more ground engaging tools 38 spaced apart across the lateral width of the frame 20, the controller 112 may be configured to determine or calculate an instantaneous or current global ground engaging tool displacement parameter for the implement 10 based on the monitored ground engaging tool displacements. Thereafter, the controller 112 may be configured to identify a soil condition for a swath of the field currently being traversed by the implement 10 based on a comparison between the determined current global ground engaging tool displacement parameter and an associated global displacement threshold.

For example, referring back to FIG. 2, one of the ground engaging tools 38 of the implement 10 may correspond a first ground engaging tool 54 configured to be pivotally coupled to the main section 42 of the frame 20, such as at a central location of the main frame 42. Similarly, the implement 10 may also include second and third ground engaging tools 56, 58 configured to be respectively pivotally coupled to the first and second wing sections 44, 46 of the frame 20, such as at central locations thereof. Additionally, the implement 10 may include fourth and fifth ground engaging tools 60, 62 configured to be pivotally coupled to the main section 42 of the frame 20 and laterally aligned with the tracks 16 of the work vehicle 12 (e.g., with tracks 16 being indicated by dashed boxes in FIG. 2). In embodiments where the work vehicle 12 includes wheels in lieu of the tracks 16, the fourth and fifth ground engaging tools 60, 62 may, instead, be laterally aligned with the wheels of the work vehicle 12. As shown, the various ground engaging tools 54, 56, 58, 60, 62 may, in one embodiment, be configured to be pivotally coupled to the forward end 22 of the frame 20, such as within a longitudinally forward-most rank of the plurality of ranks 40.

Figure 8:
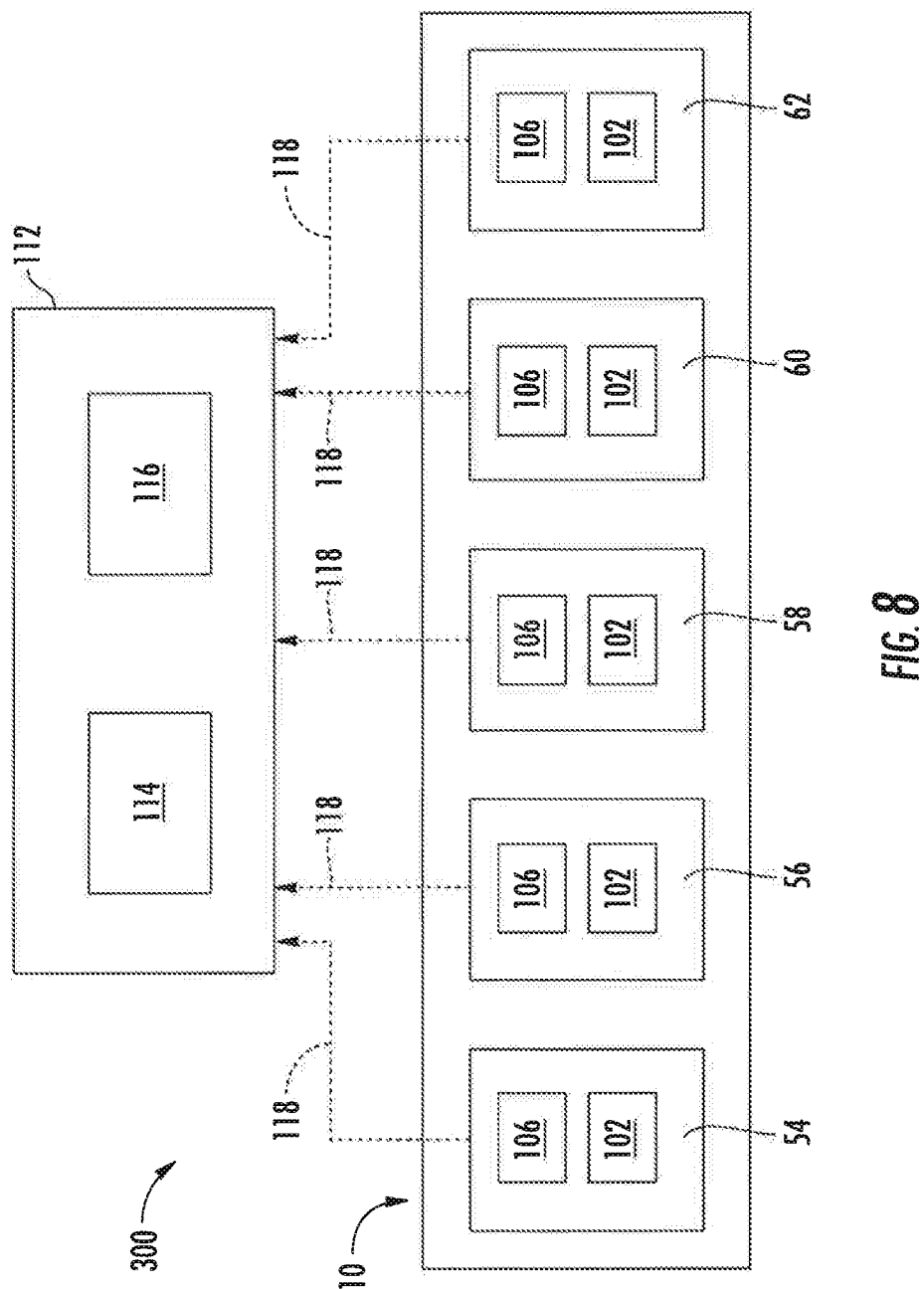
FIG. 8 illustrates a perspective view of one embodiment of a system for monitoring soil conditions within a field in accordance with aspects of the present subject matter.

Referring now to FIG. 8, a schematic view of one embodiment of a system 300 for monitoring soil conditions within a field is illustrated in accordance with aspects of the present subject matter. In general, the system 300 will be described herein with reference to the implement 10 and the ground engaging tools 54, 56, 58, 60, 62 described above with reference to FIGS. 1-2. However, it should be appreciated by those of ordinary skill in the art that the disclosed system 300 may generally be utilized with ground engaging tools having any other suitable ground engaging tool configuration and/or implements having any other suitable implement configuration.

As shown in FIG. 8, similar to the embodiments of the system 100 described above with reference to FIGS. 3 and 5, the system 300 may include a plurality of the sensors 106 communicatively coupled to an associated controller 112, with each sensor 106 being provided in operative association with one of the ground engaging tools 54, 56, 58, 60, 62 (or with its corresponding biasing element 102) to allow the sensors 106 to detect an operating parameter indicative of the current position of each ground engaging tool 54, 56, 58, 60, 62 relative to the implement's frame 20. As discussed above, each sensor 106 may correspond to a rotary sensor 108, a pressure sensor 120, or any other suitable sensor(s) or sensing device(s) that is configured to directly or indirectly detect the pivotal motion of its associated ground engaging tool 54, 56, 58, 60, 62.

In several embodiments, based on the measurement data provided by the sensors 106, the controller 112 may be configured to monitor the displacement of each ground engaging tool 54, 56, 58, 60, 62 relative to its predetermined ground engaging tool position. For instance, the controller 112 may include a look-up table or suitable mathematical formula stored within its memory 116 that correlates the sensor measurements to the displacements of the various ground engaging tools 54, 56, 58, 60, 62.

Additionally, in several embodiments, the controller 112 may also be configured to determine a current global ground engaging tool displacement parameter for the implement 10 based on the monitored displacements of the ground engaging tools 54, 56, 58, 60, 62. For example, in one embodiment, the controller 112 may be configured to compare the individual monitored displacements of the various ground engaging tools 54, 56, 58, 60, 62 to determine an instantaneous or current maximum displacement value for the ground engaging tools 54, 56, 58, 60, 62 as the implement 10 is being traversed over a portion of the field. In such an embodiment, the controller 112 may be configured to identify such instantaneous or current maximum displacement value as the current global ground engaging tool displacement parameter for the implement 10. In another embodiment, the controller 112 may be configured to calculate an instantaneous or current average displacement value for the individual monitored displacements of the ground engaging tools 54, 56, 58, 60, 62 as the implement 10 is being traversed over a given portion of the field. In such an embodiment, the controller 112 may be configured to identify such average displacement value as the current global ground engaging tool displacement parameter for the implement 10.

Moreover, the controller 112 may also be configured to identify a soil condition for the portion of the field currently being traversed by the implement 10 based on a comparison between the current global ground engaging tool displacement parameter and a predetermined global displacement threshold associated with the implement 10. For instance, the controller 112 may be configured to compare the current global ground engaging tool displacement parameter determined for the implement 10 to the associated global displacement threshold. In such instances, when the current global ground engaging tool displacement parameter exceeds the predetermined global displacement threshold (e.g., thereby indicating that the ground engaging tool displacement of one or more of the ground engaging tools 54, 56, 58, 60, 62 is greater than desired), the controller 112 may be configured to indicate that the portion of the field currently being traversed by the implement 10 has a first soil condition, such as a compacted or firm soil condition. Conversely, when the current global ground engaging tool displacement parameter falls below the predetermined global displacement threshold, the controller 112 may be configured to indicate that the portion of the field currently being traversed by the implement 10 has a second soil condition, such as a loose or uncompacted soil condition. Additionally, in one embodiment, the controller 112 may be configured to generate a field map that visually identifies the soil conditions for the field across each portion of the field traversed by the implement 10.

It should be appreciated that the controller 112 determines the current global ground engaging tool displacement parameter and identifies the corresponding soil condition continuously as the implement 10 traverses the field. For example, the controller 112 may determine the current global ground engaging tool displacement parameter and the corresponding soil condition once a predetermined time interval has elapsed (e.g., every 0.1 second, or every 0.5 second, or every 1 seconds, etc.). In this respect, controller 112 is able to identify location-specific changes in the soil condition as the implement is traversed across the field.

In several embodiments, when it is determined that the current global ground engaging tool displacement parameter for the implement 10 exceeds the predetermined global displacement threshold, the controller 112 may be configured to initiate a global control action associated with reducing the displacement of the ground engaging tools 54, 56, 58, 60, 62. For instance, in one embodiment, the controller 112 may be configured to transmit a notification to the operator of the implement 10 (e.g., by causing a visual or audible notification or indicator to be presented to the operator within the work vehicle 12) that provides an indication that the current global ground engaging tool displacement parameter has exceeded the predetermined global displacement threshold. In such instances, the operator may then choose to initiate any suitable corrective action he/she believes is necessary, such as by reducing the ground speed of the implement 10 and/or the work vehicle 12. Alternatively, the controller 112 may be configured to automatically control the operation of one or more components of the implement and/or the work vehicle 12 (e.g., the vehicle's engine or transmission) in a manner that reduces the ground speed of the implement 10 and/or the work vehicle 12 when the current global ground engaging tool displacement parameter exceeds the predetermined global displacement threshold, such as by reducing or limiting the engine power output. In even further embodiments, the controller 112 may be configured to initiate any other suitable control action. For instance, as described above with reference to FIG. 6, the controller 112 may be configured to automatically adjust the down pressure exerted on the ground engaging tools 54, 56, 58, 60, 62 so as to reduce the displacement defined between the current position of the ground engaging tools 54, 56, 58, 60, 62 and the predetermined ground engaging tool position.

Additionally, in several embodiments, the controller 112 may also be configured to determine a global soil condition for the field. In general, the global soil condition may provide an indication of the overall quality of the field, such as that the soil condition for the field is "good" or "bad." For instance, the controller 112 may be configured to determine a percentage of the field traversed by the implement 10 across which the current global ground engaging tool displacement parameter exceeded the predetermined global displacement threshold. The controller 112 may then compare the identified percentage of the field to an associated threshold value to determine the global soil condition for the field. For instance, if the identified percentage exceeds the associated threshold value, the overall soil condition for the field may be classified as "bad"; whereas, if the identified percentage is less than the associated threshold value, the overall soil condition for the field may be classified as "good." In another embodiment, the controller 112 may be configured to determine the number of times that the current global ground engaging tool displacement parameter exceeded the predetermined global displacement threshold as the implement 10 was being pulled across the field. Thereafter, the controller 112 may compare the identified number of times to an associated threshold value to determine the global level soil condition for the field. For instance, if the identified number exceeds the associated threshold value, the overall soil condition for the field may be classified as "bad"; whereas, if the identified number is less than the associated threshold value, the overall soil condition for the field may be classified as "good."

Additionally, in one embodiment, the controller 112 may also be configured to determine when a ground engaging tool float event is occurring based on the global ground engaging tool displacement parameter (as opposed to making such a determination based on the individual displacement of a given ground engaging tool). For instance, the controller 112 may be configured to identify a time period across which the current global ground engaging tool displacement parameter exceeds the predetermined global displacement threshold. The controller 112 may then compare the identified time period to an associated threshold time period. Thereafter, assuming that the identified time period exceeds the threshold time period, the controller 112 may determine that a ground engaging tool float event is occurring during operation of the implement 10.

Figure 9:
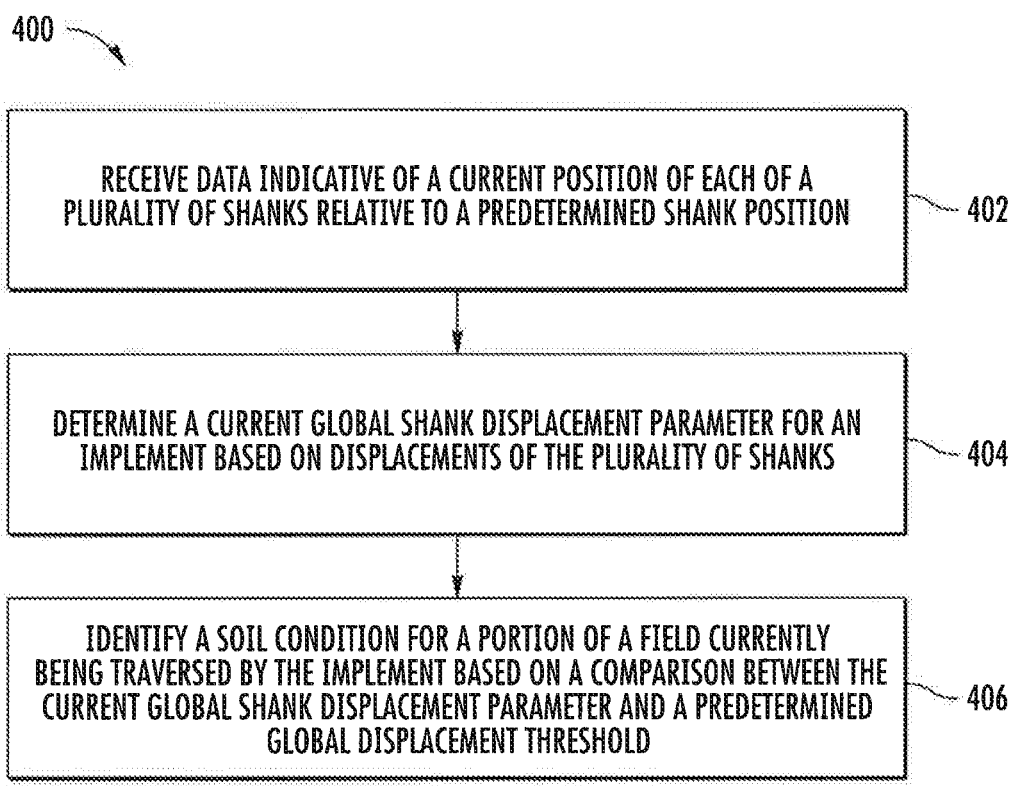
FIG. 9 illustrates a flow diagram of one embodiment of a method for monitoring soil conditions within a field in accordance with aspects of the present subject matter.

Referring now to FIG. 9, a flow diagram of one embodiment of a method 400 for monitoring soil conditions within a field is illustrated in accordance with aspects of the present subject matter. In general, the method 400 will be described herein with reference to the implement 10, the ground engaging tools 38, 54, 56, 58, 60, 62, and the system 300 described above with reference to FIGS. 1-8. However, it should be appreciated by those of ordinary skill in the art that the disclosed method 400 may generally be utilized to monitor soil conditions using any agricultural implement having any suitable implement configuration and/or any ground engaging tool having any suitable ground engaging tool configuration. In addition, although FIG. 9 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 9, at (402), the method 400 may include receiving data indicative of a current position of each of a plurality of ground engaging tools relative to a predetermined ground engaging tool position. For instance, as indicated above, the controller 112 may be communicatively coupled to a plurality of sensors 106, with each sensor being configured to monitor an operating parameter indicative of the current position of a corresponding ground engaging tool 54, 56, 58, 60, 62. In such an embodiment, the measurement signals 118 transmitted from each sensor 106 may be received by the controller 112 for monitoring the current position and/or displacement of each associated ground engaging tool.

Additionally, at (404), the method 400 may include determining a current global ground engaging tool displacement parameter for the implement based on the monitored displacements of the ground engaging tools. For instance, as indicated above, the controller 112 may, in one embodiment, be configured to determine the current global ground engaging tool displacement parameter for the implement 10 by identifying the instantaneous or current maximum displacement value of the various monitored ground engaging tool displacements. In another embodiment, the controller 112 may be configured to determine the current global ground engaging tool displacement parameter for the implement 10 by calculating an instantaneous or average displacement value for the various monitored ground engaging tool displacements.

Moreover, at (406), the method 400 may include identifying a soil condition for a portion of the field currently being traversed by the implement based on a comparison between the current global ground engaging tool displacement parameter and a predetermined global displacement threshold set for the implement. For instance, as indicated above, if the current global ground engaging tool displacement parameter exceeds the predetermined global displacement threshold, the controller 112 may identify that the portion of the field currently being traversed by the implement 10 has a first soil condition, such as a compacted or hardened soil condition. Alternatively, if the current global ground engaging tool displacement parameter is less than predetermined global displacement threshold, the controller 112 may identify that the portion of the field currently being traversed by the implement 10 has a second soil condition, such as a soft or loosened soil condition. Moreover, in several embodiments, the controller 112 may also generate a field map that visually identifies the soil conditions for the field across each portion of the field traversed by the implement 10.

In several embodiments, the method 400 may also include determining a global soil condition for the field. For instance, the controller 112 determine a percentage of the field traversed by the implement across which the current global ground engaging tool displacement parameter exceeded the predetermined global displacement threshold and compare the identified percentage to an associated threshold value to determine a global soil condition for the field. In another embodiment, the controller 112 may determine a number of times that the current global ground engaging tool displacement parameter exceeded the predetermined global displacement threshold and compare the identified number of times to an associated threshold value to determine a global soil condition for the field.

The method 400 may also include initiating a control action associated with reducing the displacement of the ground engaging tools when the global ground engaging tool displacement parameter exceeds the predetermined displacement threshold. For instance, the controller 112 may initiate a control action associated with reducing the displacement of the ground engaging tools 54, 56, 58, 60, 62 when the global ground engaging tool displacement parameter exceeds the predetermined displacement threshold.

This written description uses examples to disclose the technology, including the best mode, and also to enable any person skilled in the art to practice the technology, including making and using any devices or systems and performing any incorporated methods. The patentable scope of the technology is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

What is claimed is:

1. A system for monitoring soil conditions within a field, the system comprising:
   an agricultural implement configured to be traversed across a field, the implement including a frame extending laterally between a first side and a second side, the implement further including a plurality of ground engaging tools pivotally coupled to the frame, the ground engaging tools being spaced apart from one another laterally between the first and second sides of the frame, the implement further including a plurality of biasing elements, each biasing element being coupled between the frame and a corresponding ground engaging tool of the plurality of ground engaging tools and being configured bias the corresponding ground engaging tool to a predetermined ground engaging tool position relative to the frame;
   a plurality of sensors, each sensor being configured to detect a parameter indicative of a current position of one of the plurality of ground engaging tools relative to the predetermined ground engaging tool position; and
   a controller communicatively coupled to the plurality of sensors, the controller being configured to:
   monitor a displacement of each ground engaging tool relative to the predetermined ground engaging tool position based on sensor measurements provided by the plurality of sensors;
   determine a current global ground engaging tool displacement parameter for the implement based on the monitored displacements of the plurality of ground engaging tools; and
   identify a soil condition for a swath of the field being traversed by the implement based on a comparison between the current global ground engaging tool displacement parameter and a predetermined global displacement threshold.

2. The system of claim 1, wherein the current global ground engaging tool displacement parameter corresponds to a current maximum displacement value of the monitored displacements of the plurality of ground engaging tools.

3. The system of claim 1, wherein the current global ground engaging tool displacement parameter corresponds to a current average displacement value of the monitored displacements of the plurality of ground engaging tools.

4. The system of claim 1, wherein the controller is further configured to generate a field map that visually identifies the soil conditions for the field across each swath traversed by the implement.

5. The system of claim 1, wherein the controller is further configured to initiate a control action associated with reducing the displacement of the ground engaging tools when the current global ground engaging tool displacement parameter exceeds the predetermined global displacement threshold.

6. The system of claim 5, wherein the control action is associated with notifying an operator of the implement when the current global ground engaging tool displacement parameter exceeds the predetermined global displacement threshold.

7. The system of claim 5, wherein the control action is associated with reducing a ground speed of the implement when the current global ground engaging tool displacement parameter exceeds the predetermined global displacement threshold.

8. The system of claim 1, wherein the controller is further configured to determine a percentage of the field traversed by the implement where the current global ground engaging tool displacement parameter exceeds the predetermined global displacement threshold and compare the identified percentage to an associated threshold value of the field to determine a global soil condition for the field.

9. The system of claim 1, wherein the controller is further configured to determine a number of times that the current global ground engaging tool displacement parameter exceeds the predetermined global displacement threshold and compare the identified number of times to an associated threshold value to determine a global soil condition for the field.

10. The system of claim 1, wherein the controller is further configured to identify a time period across which the current global ground engaging tool displacement parameter exceeds the predetermined global displacement threshold and compare the identified time period to a threshold time period to determine when a ground engaging tool float event is occurring during operation of the implement.

11. The system of claim 1, wherein the frame comprises a main section and a plurality of wing sections coupled to the main section, each section including at least one ground engaging tool of the plurality of ground engaging tools and at least one sensor of the plurality of sensors.

12. The system of claim 1, wherein the implement is configured to be towed by a work vehicle across the field, the implement including first and second ground engaging tools of the plurality of ground engaging tools, the first and second ground engaging tool being configured to be laterally aligned with first and second wheels or first and second tracks of the work vehicle.

13. A method for monitoring soil conditions within a field during operation of an agricultural implement, the implement including a frame extending laterally between a first side and a second side, the implement further including a plurality of ground engaging tools pivotally coupled to the frame, the ground engaging tools being spaced apart from one another laterally between the first and second sides of the frame, the implement further including a plurality of biasing elements, each biasing element being coupled between the frame and a corresponding ground engaging tool of the plurality of ground engaging tools and being configured bias the corresponding ground engaging tool to a predetermined ground engaging tool position relative to the frame, the method comprising:

receiving, with a computing device, data indicative of a current position of each of the plurality of ground engaging tools relative to a predetermined ground engaging tool position;

determining, with the computing device, a current global ground engaging tool displacement parameter for the implement based on the displacements of the plurality of ground engaging tools; and identifying, with the computing device, a soil condition for a swath of the field being traversed by the implement based on a comparison between the current global ground engaging tool displacement parameter and a predetermined global displacement threshold.

14. The method of claim 13, wherein determining the current global ground engaging tool displacement parameter comprises identifying a current maximum displacement value of the displacements of the plurality of ground engaging tools.

15. The method of claim 13, wherein determining the current global ground engaging tool displacement parameter comprises calculating a current average displacement value of the displacements of the plurality of ground engaging tools.

16. The method of claim 13, further comprising:
generating, by the computing device, a field map that visually identifies the soil conditions for the field across each swath traversed by the implement.

17. The method of claim 13, further comprising:
initiating, by the computing device, a control action associated with reducing the displacement of the ground engaging tools when the current global ground engaging tool displacement parameter exceeds the predetermined global displacement threshold.

18. The method of claim 13, further comprising:
determining, with the computing device, a percentage of the field traversed by the implement where the current global ground engaging tool displacement parameter exceeds the predetermined global displacement threshold; and
comparing, with the computing device, the identified percentage to an associated threshold value to determine a global soil condition for the field.

19. The method of claim 13, further comprising:
determining, with the computing device, a number of times that the current global ground engaging tool displacement parameter exceeds the predetermined global displacement threshold; and
comparing, with the computing device, the identified number of times to an associated threshold value to determine a global soil condition for the field.

20. The method of claim 13, further comprising:
identifying, with the computing device, a time period across which the current global ground engaging tool displacement parameter exceeds the predetermined global displacement threshold; and
comparing, with the computing device, the identified time period to a threshold time period to determine when a ground engaging tool float event is occurring during operation of the implement.

* * * * *